United States Patent
Schmainda

(10) Patent No.: US 6,807,441 B2
(45) Date of Patent: Oct. 19, 2004

(54) EVALUATION OF TUMOR ANGIOGENESIS USING MAGNETIC RESONANCE IMAGING

(75) Inventor: Kathleen M. Schmainda, Wauwatosa, WI (US)

(73) Assignee: The MCW Research Foundation Inc., Milwaukee, WI (US)

(*) Notice: Subject to any disclaimer, the term of this patent is extended or adjusted under 35 U.S.C. 154(b) by 432 days.

(21) Appl. No.: 09/861,220

(22) Filed: May 18, 2001

(65) Prior Publication Data

US 2002/0026116 A1 Feb. 28, 2002

Related U.S. Application Data

(60) Provisional application No. 60/205,850, filed on May 19, 2000.

(51) Int. Cl.[7] ............................. A61B 5/03; A61B 5/05
(52) U.S. Cl. ..................................... 600/424; 600/419
(58) Field of Search ............................... 600/424, 407, 600/419, 410, 425, 411; 606/20, 27, 32, 2; 324/307, 308, 309

(56) References Cited

U.S. PATENT DOCUMENTS

| | | | | |
|---|---|---|---|---|
| 4,733,188 A | * | 3/1988 | Sekihara et al. | 324/312 |
| 5,170,121 A | * | 12/1992 | Ogikubo et al. | 324/307 |
| 5,352,979 A | * | 10/1994 | Conturo | 324/307 |
| 5,565,777 A | * | 10/1996 | Kanayama et al. | 324/309 |
| 5,685,305 A | * | 11/1997 | Moonen et al. | 600/419 |
| 5,798,642 A | * | 8/1998 | Watanabe | 324/307 |
| 6,023,634 A | * | 2/2000 | Hanawa et al. | 600/410 |
| 6,066,950 A | * | 5/2000 | Tsukamoto et al. | 324/309 |
| 6,321,105 B1 | * | 11/2001 | Jenkins et al. | 600/407 |
| 6,584,337 B2 | * | 6/2003 | Dumoulin et al. | 600/410 |

OTHER PUBLICATIONS

Simultaneous Gradient–Echo/Spin–Echo EPI of Graded Ischemia in Human Skeletal Muscle: JMRI 1998; 8:1106–1113; Kathleen M. Donahue, et al.

Spin–Echo and Gradient–Echo EPI Human Brain Activation using BOLD Contrast: a Comparative Study at 1.5T; NMR in Medicine, vol. 7, 12–20 (1994), Peter A. Bandettini, et al.

MR Contrast due to Intravascular Magnetic Susceptibility Perturbation; MRM 34:555–566 (1995) Jerrold J. Boxerman, et al.

NMR Imaging of Changes in Vascular Morphology Due To Tumor Angiogenesis; MRM 40:793–799 (1998); Joelle Dennie, et al.

SMRM (1994); R. M. Weisskoff, et al.

* cited by examiner

Primary Examiner—Daniel Robinson
(74) Attorney, Agent, or Firm—Quarles & Brady LLP

(57) ABSTRACT

Two sets of time course NMR data are acquired using an EPI pulse sequence in which both gradient recalled echo NMR signals and spin-echo NMR signals are acquired after bolus injection of a contrast agent. The gradient-echo signals and spin-echo NMR signals are employed to calculate rCBV maps which are corrected for contrast leakage and used as a measure of tumor angiogenesis. Both the gradient echo and spin echo signals are employed to calculate a $\Delta R2$ weighting ratio which is also a measure of tumor angiogenesis.

7 Claims, 3 Drawing Sheets

EVALUATION OF TUMOR ANGIOGENESIS USING MAGNETIC RESONANCE IMAGING

CROSS-REFERENCE TO RELATED APPLICATIONS

This application is based upon Provisional Application Ser. No. 60/205,850 filed on May 19, 2000.

BACKGROUND OF THE INVENTION

The field of the invention is magnetic resonance imaging (MRI), and particularly, the imaging of tumors in the human brain.

In the United states, approximately 17,000 new patients are diagnosed each year with a primary intracranial neoplasm. Approximately 60% of these tumors are malignant, and gliomas are the most common type. Although there is a wide variability in life expectancy for patients with the various subtypes of gliomas, their prognosis is generally poor. This is especially true for those with high-grade gliomas, in spite of treatment modalities such as surgery, radiation therapy and chemotherapy. The most aggressive gliomas are those characterized by angiogenesis, a process of new vessel growth essential for the progression of the tumor from low-grade to high-grade. There is also a clear correlation between increased vascularity of the tumor and increased malignancy. Given the vascular nature of these tumors and the lack of success with standard cancer treatments, there is both a great need and hope for therapies that inhibit angiogenesis. Now that several of these agents are entering clinical trials an assessment of their ability to inhibit angiogenesis is crucial to evaluating their clinical potential.

Contrast-enhanced conventional MRI methods have become the imaging standard for the depiction and detection of brain tumors. However, these post-contrast, steady-state methods do not provide reliable information about tumor angiogenesis. The tumor signal enhancement volume that is measured by these prior methods depends on the status of the blood-brain barrier, which is affected by both tumor type and prior treatments for the disease. In addition, a tumor's response to an anti-angiogenic therapy can occur before effects on tumor volume can be detected, or may even occur with increases in tumor volume that result from the evolution of local necroses. Finally, an anti-angiogenic therapy may be judged successful, not necessarily because it results in tumor shrinkage, but because it stabilizes the tumor or returns it to a dormant state. For these reasons, non-invasive methods that can more specifically monitor vessel growth and regression in tumors are needed for the evaluation of anti-angiogenic therapies.

In an effort to provide more direct measures of tumor angiogenesis, relative cerebral blood volume (rCBV) information from dynamic susceptibility-contrast studies have been acquired using MRI methods. Preliminary findings suggest that MRI-acquired rCBV may better differentiate histologic tumor types than prior conventional MRI methods and provide information to predict glial tumor grade. In these rCBV studies, either gradient-echo (GE) or spin-echo (SE) pulse sequences are used to monitor the MR signal intensity during the passage of contrast agent. Each method is sensitive to a different population of blood vessels. Specifically, while GE transverse magnetization relaxation rate changes are sensitive to blood vessels of all sizes, SE transverse magnetization relaxation rate changes are more sensitive to capillary-sized blood vessels. Microvessel density is a recognized marker of tumor angiogenesis in invasive human cancers such as breast and prostate and it has a demonstrated prognostic value in brain tumors. It has been suggested, therefore, that SE-derived rCBV may best correlate with brain tumor angiogenesis.

A difficulty with using first pass contrast-enhanced MRI rCBV techniques to study brain tumors is the leakage which occurs when small molecular weight Gd agents are used. When acquiring data during the first pass of such a Gd contrast agent, the susceptibility effect dominates the signal if the Gd contrast agent remains contained in the vasculature. This is the case when the blood brain barrier is intact. However, with significant blood brain barrier disruption, as if often the case with brain tumors, contrast agent leaks out of the vasculature into the brain or tumor tissue resulting in enhanced T1 relaxation effects outside the vasculature. The resulting MRI signal increase due to T1 effects masks signal decrease due to T2 effects leading to an underestimation of rCBV.

SUMMARY OF THE INVENTION

The present invention relates to the production of MR images which correlate with brain tumor angiogenesis. More particularly, images are acquired during first passage of a contrast agent using a pulse sequence which acquires both gradient-echo NMR signals and spin-echo NMR signals, calculating a relative cerebral blood volume image (rCBV) using images reconstructed with both the gradient-echo and spin-echo NMR signals, and correcting the rCBV image for leakage of contrast agent out of the imaged vasculature. Another aspect of the invention is the production of a $T_2$ relaxation rate image ($\Delta R2^*$) from the gradient-echo NMR signals, producing a $T_2$ relaxation rate image ($\Delta R2$) from the spin-echo NMR signals, and producing a ratio map image by calculating the ratio $\Delta R2^*/\Delta R2$ of corresponding pixels in the respective $\Delta R2^*$ and $\Delta R2$ images.

A general object of the invention is to produce images with which the progression of brain tumors from low grade to high grade can be measured. It has been discovered that the corrected rCBV images derived from the gradient-echo and spin-echo NMR signals as well as the ratio map image ($\Delta R2^*/\Delta R2$) correlate strongly with tumor grade.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
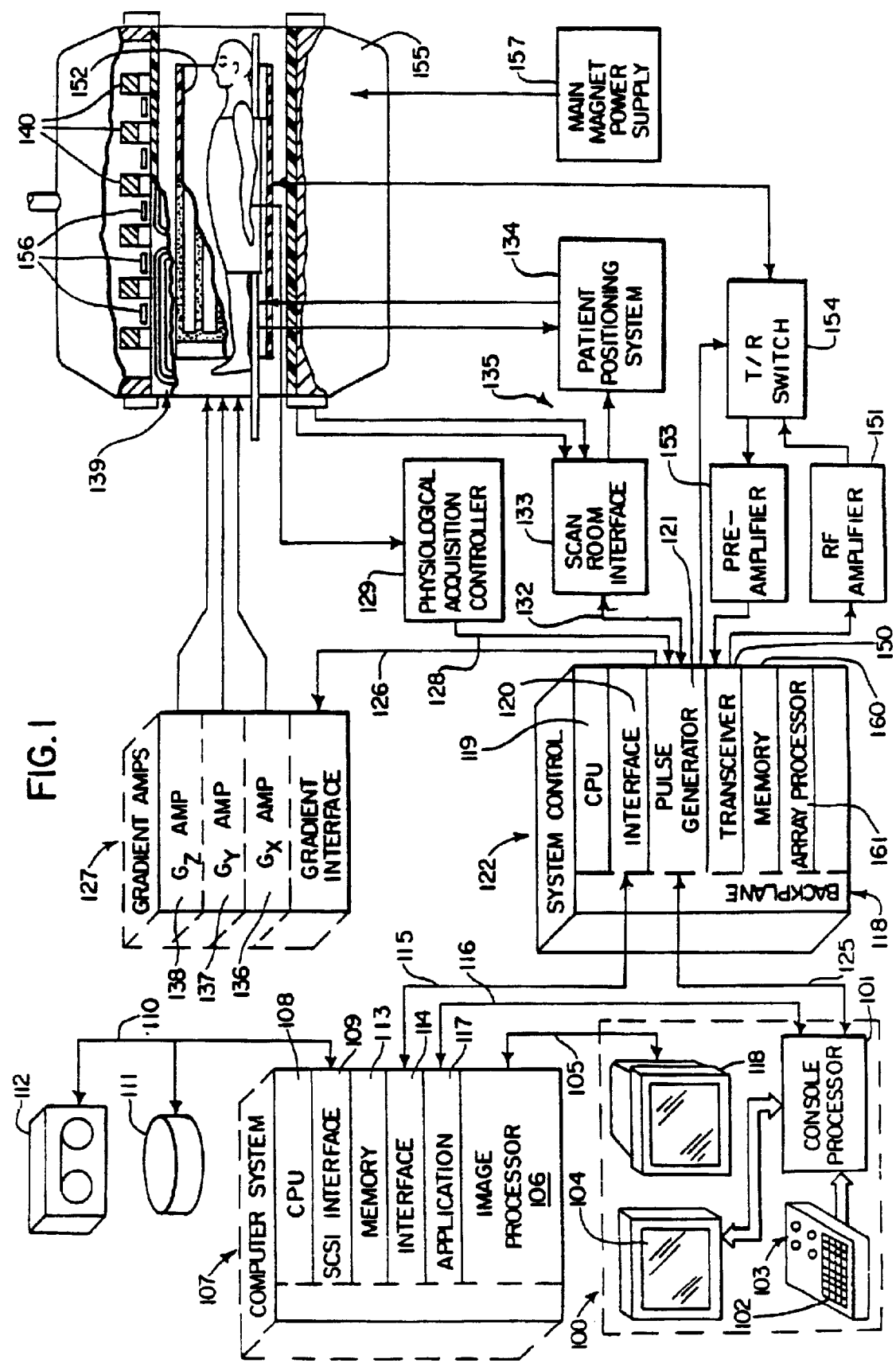
FIG. 1 is a block diagram of an NMR system which employs the present invention.

Referring first to FIG. 1, there is shown the major components of a preferred NMR system which incorporates the present invention and which is sold by the General Electric Company under the trademark "SIGNA". The operation of the system is controlled from an operator console 100 which includes a console processor 101 that scans a keyboard 102 and receives inputs from a human operator through a control panel 103 and a plasma display/touch screen 104. The console processor 101 communicates through a communications link 116 with an applications interface module 117 in a separate computer system 107. Through the keyboard 102 and controls 103, an operator controls the production and display of images by an image processor 106 in the computer system 107, which connects directly to a video display 118 on the console 100 through a video cable 105.

The computer system 107 is formed about a backplane bus which conforms with the VME standards, and it includes a number of modules which communicate with each other through this backplane. In addition to the application interface 117 and the image processor 106, these include a CPU module 108 that controls the VME backplane, and an SCSI interface module 109 that connects the computer system 107 through a bus 110 to a set of peripheral devices, including disk storage 111 and tape drive 112. The computer system 107 also includes a memory module 113, known in the art as a frame buffer for storing image data arrays, and a serial interface module 114 that links the computer system 107 through a high speed serial link 115 to a system interface module 120 located in a separate system control cabinet 122.

The system control 122 includes a series of modules which are connected together by a common backplane 118. The backplane 118 is comprised of a number of bus structures, including a bus structure which is controlled by a CPU module 119. The serial interface module 120 connects this backplane 118 to the high speed serial link 115, and pulse generator module 121 connects the backplane 118 to the operator console 100 through a serial link 125. It is through this link 125 that the system control 122 receives commands from the operator which indicate the scan sequence that is to be performed.

The pulse generator module 121 operates the system components to carry out the desired scan sequence. It produces data which indicates the timing, strength and shape of the RF pulses which are to be produced, and the timing of and length of the data acquisition window. The pulse generator module 121 also connects through serial link 126 to a set of gradient amplifiers 127, and it conveys data thereto which indicates the timing and shape of the gradient pulses that are to be produced during the scan. The pulse generator module 121 also receives patient data through a serial link 128 from a physiological acquisition controller 129. The physiological acquisition control 129 can receive a signal from a number of different sensors connected to the patient. For example, it may receive ECG signals from electrodes or respiratory signals from a bellows and produce pulses for the pulse generator module 121 that synchronizes the scan with the patient's cardiac cycle or respiratory cycle. And finally, the pulse generator module 121 connects through a serial link 132 to scan room interface circuit 133 which receives signals at inputs 135 from various sensors associated with the position and condition of the patient and the magnet system. It is also through the scan room interface circuit 133 that a patient positioning system 134 receives commands which move the patient cradle and transport the patient to the desired position for the scan.

The gradient waveforms produced by the pulse generator module 121 are applied to a gradient amplifier system 127 comprised of $G_x$, $G_y$ and $G_z$ amplifiers 136, 137 and 138, respectively. Each amplifier 136, 137 and 138 is utilized to excite a corresponding gradient coil in an assembly generally designated 139. The gradient coil assembly 139 forms part of a magnet assembly 155 which includes a polarizing magnet 140 that produces a 1.5 Tesla polarizing field that extends horizontally through a bore. The gradient coils 139 encircle the bore, and when energized, they generate magnetic fields In the same direction as the main polarizing magnetic field, but with gradients $G_x$, $G_y$ and $G_z$ directed in the orthogonal x-, y- and z-axis directions of a Cartesian coordinate system. That is, if the magnetic field generated by the main magnet 140 is directed in the z direction and is termed BO, and the total magnetic field in the z direction is referred to as $B_z$, then $G_x = \partial B_z/\partial x$, $G_y = \partial B_z/\partial y$ and $G_z = \partial B_z/\partial z$, and the magnetic field at any point (x,y,z) in the bore of the magnet assembly 141 is given by $B(x,y,z) = B_O + G_x x + G_y y G_z z$. The gradient magnetic fields are utilized to encode spatial information into the NMR signals emanating from the patient being scanned. Because the gradient fields are switched at a very high speed when an EPI sequence is used to practice the preferred embodiment of the invention, local gradient coils are employed in place of the whole-body gradient coils 139. These local gradient coils are designed for the head and are in close proximity thereto. This enables the inductance of the local gradient coils to be reduced and the gradient switching rates increased as required for the EPI pulse sequence. For a description of these local gradient coils which is incorporated herein by reference, see U.S. Pat. No. 5,372,137 issued on Dec. 13, 1994 and entitled "NMR Local Coil For Brain Imaging".

Located within the bore 142 is a circular cylindrical whole-body RF coil 152. This coil 152 produces a circularly polarized RF field in response to RF pulses provided by a transceiver module 150 in the system control cabinet 122. These pulses are amplified by an RF amplifier 151 and coupled to the RF coil 152 by a transmit/receive switch 154 which forms an integral part of the RF coil assembly. Waveforms and control signals are provided by the pulse generator module 121 and utilized by the transceiver module 150 for RF carrier modulation and mode control. The resulting NMR signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150.

The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate local RF head coil to be used in the transmit and receive mode to improve the signal-to-noise ratio of the received NMR signals. With currently available NMR systems such a local RF coil is preferred in order to detect small variations in NMR signal. Reference is made to the above cited U.S. Pat. No. 5,372,137 for a description of the preferred local RF coil.

In addition to supporting the polarizing magnet 140 and the gradient coils 139 and RF coil 152, the main magnet assembly 141 also supports a set of shim coils 156 associated with the main magnet 140 and used to correct inhomogeneities in the polarizing magnet field. The main power supply 157 is utilized to bring the polarizing field produced by the superconductive main magnet 140 to the proper operating strength and is then removed.

The NMR signals picked up by the RF coil are digitized by the transceiver module 150 and transferred to a memory module 160 which is also part of the system control 122.

When the scan is completed and an entire array of data has been acquired in the memory modules 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the video display 118 as will be described in more detail hereinafter.

Figure 2:
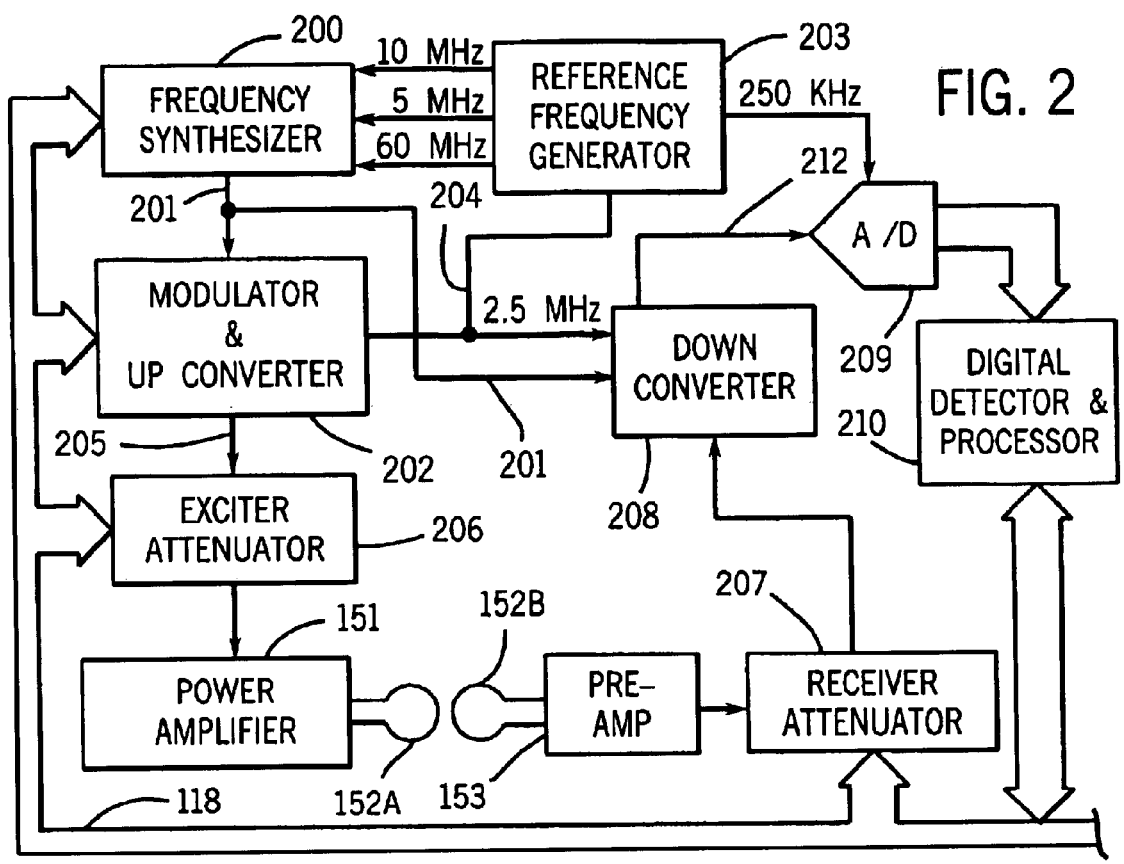
FIG. 2 is an electrical block diagram of the transceiver which forms part of the NMR system of FIG. 1.

Referring particularly to FIGS. 1 and 2, the transceiver 150 includes components which produce the RF excitation field B1 through power amplifier 151 at a coil 152A and components which receive the resulting NMR signal induced in a coil 152B. As indicated above, the coils 152A and B may be a single whole-body coil, but the best results are achieved with a single local RF coil specially designed for the head. The base, or carrier, frequency of the RF excitation field is produced under control of a frequency synthesizer 200 which receives a set of digital signals (CF) through the backplane 118 from the CPU module 119 and pulse generator module 121. These digital signals indicate the frequency and phase of the RF carrier signal which is produced at an output 201. The commanded RF carrier is applied to a modulator and up converter 202 where its amplitude is modulated in response to a signal R(t) also received through the backplane 118 from the pulse generator module 121. The signal R(t) defines the envelope, and therefore the bandwidth, of the RF excitation pulse to be produced. It is produced in the module 121 by sequentially reading out a series of stored digital values that represent the; desired envelope. These stored digital values may, in turn, be changed from the operator console 100 to enable any desired RF pulse envelope to be produced. The modulator and up converter 202 produces an RF pulse at the desired Larmor frequency at an output 205. The magnitude of the RF excitation pulse output through line 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIG. 1 and 2 the NMR signal produced by the subject is picked up by the receiver coil 152B and applied through the preamplifier 153 to the input of a receiver attenuator 207. The receiver attenuator 207 further amplifies the NMR signal and this is attenuated by an amount determined by a digital attenuation signal (RA) received from the backplane 118. The receive attenuator 207 is also turned on and off by a signal from the pulse generator module 121 such that it is not overloaded during RF excitation. The received NMR signal is at or around the Larmor frequency, which in the preferred embodiment is around 63.86 MHz for 1.5 Tesla. This high frequency signal is down converted in a two step process by a down converter 208 which first mixes the NMR signal with the carrier signal on line 201 and then mixes the resulting difference signal with the 2.5 MHz reference signal on line 204. The resulting down converted NMR signal on line 212 has a maximum bandwidth of 125 kHz and it is centered at a frequency of 187.5 kHz. The down converted NMR signal is applied to the input of an analog-to-digital (A/D) converter 209 which samples and digitizes the analog signal at a rate of 250 kHz. The output of the A/D converter 209 is applied to a digital detector and signal processor 210 which produce 16-bit in-phase (I) values and 16-bit quadrature (Q) values corresponding to the received digital signal. The resulting stream of digitized I and Q values of the received NMR signal is output through backplane 118 to the memory module 160 where they are employed to reconstruct an image.

To preserve the phase information contained in the received NMR signal, both the modulator and up converter 202 in the exciter section and the down converter 208 in the receiver section are operated with common signals. More particularly, the carrier signal at the output 201 of the frequency synthesizer 200 and the 2.5 MHz reference signal at the output 204 of the reference frequency generator 203 are employed in both frequency conversion processes. Phase consistency is thus maintained and phase changes in the detected NMR signal accurately indicate phase changes produced by the excited spins. The 2.5 MHz reference signal as well as 5, 10 and 60 MHz reference signals are produced by the reference frequency generator 203 from a common 20 MHz master clock signal. The latter three reference signals are employed by the frequency synthesizer 200 to produce the carrier signal on output 201. For a more detailed description of the receiver, reference is made to U.S. Pat. No. 4,992,736 which is incorporated herein by reference.

Figure 3:
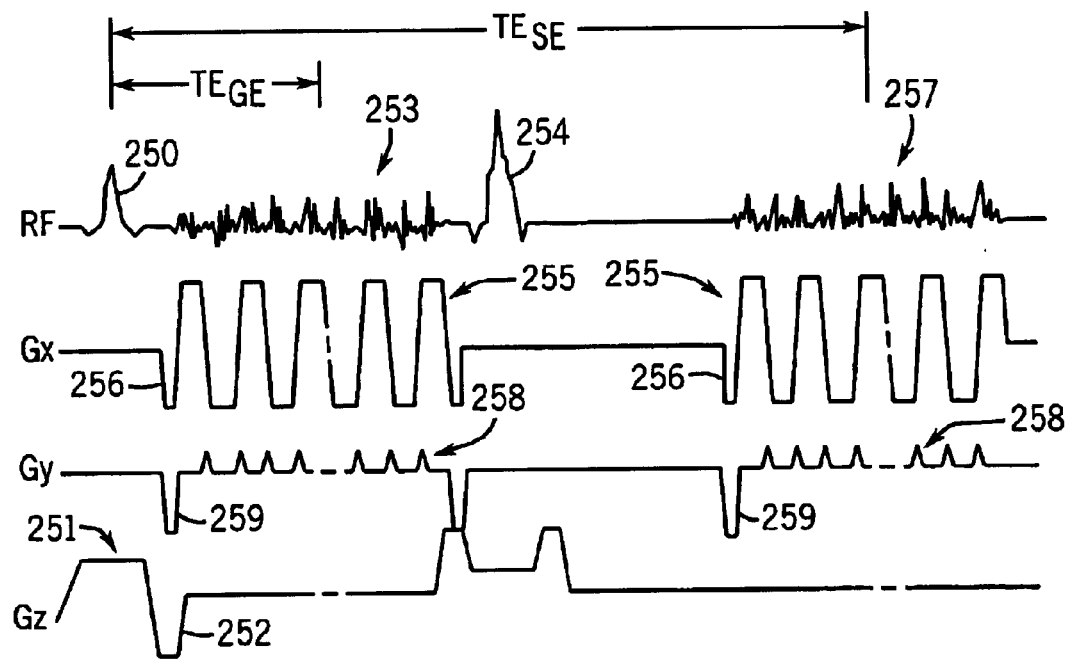
FIG. 3 is a graphic representation of the EPI pulse sequence used to practice the present invention on the NMR system of FIG. 1.

The EPI pulse sequence employed in the preferred embodiment of the invention is illustrated in FIG. 3. A 90° RF excitation pulse 250 is applied in the presence of a Gz slice select gradient pulse 251 to produce transverse magnetization in a slice through the brain. The excited spins are rephased by a negative lobe 252 on the slice select gradient Gz and then a time interval elapses before the readout sequence begins. A total of 64 separate NMR gradient recalled echo signals, indicated generally at 253, are acquired during the first part of the readout sequence. Each NMR gradient-recalled echo signal 253 is a different view which is separately phase encoded to scan $k_y$-space from $k_y=-32$ to $k_y=+32$ in monotonic order. The readout sequence is positioned such that the view acquired at ky=0 occurs at the desired echo time TEGE. The NMR signals 253 are referred to hereinafter as the GE NMR signals 253.

Following the readout of the GE NMR signals 253 a 180° RF refocusing pulse 254 is applied to invert the transverse spin magnetization and cause it to refocus at a second desired echo time $TE_{SE}$. A total of 64 separate NMR spin echo signals, indicated generally at 257, are acquired during this second part of the readout sequence. Each NMR spin echo signal 257 is a different view which is separately phase encoded to scan ky-space from ky=−32 to ky=+32 in monotonic order. The readout sequence is positioned such that the view acquired at ky=0 occurs at the desired spin echo time $TE_{SE}$. The NMR spin echo signals 257 are referred to hereinafter as the SE NMR signals 257.

The NMR echo signals 253 and 257 are acquired in the presence of an oscillating $G_x$ readout gradient field 255. Each readout sequence is started with a negative readout gradient lobe 256 and the echo signals 253 and 257 are produced as the readout gradient 255 oscillates between positive and negative values. A total of 64 samples are taken of each NMR echo signal 253 or 257 during each readout gradient pulse 255. The successive NMR echo signals 253 and 257 are separately phase encoded by a series of $G_y$ phase encoding gradient pulses 258. The first gradient pulse is a negative lobe 259 that occurs before the echo signals are acquired to encode the first view at $k_y=-32$. Subsequent phase encoding pulses 258 occur as the readout gradient pulses 255 switch polarity, and they step the phase encoding monotonically upward through $k_y$ space.

At the completion of the EPI pulse sequence, therefore, 64 separate frequency encoded samples of 64 separately phase encoded GE NMR signals 253 and SE NMR signals 257 have been acquired. Each 64×64 element arrays of complex numbers is Fourier transformed along both of its dimensions ($k_y$ and $k_x$) to produce a 64×64 element array of image data that indicates the NMR signal magnitude along each of its two dimensions (y and x). As explained above, a two dimensional Fourier transformation is performed by the array processor 161 (FIG. 1) and each resulting NMR image data set is stored in the disk 111 for further processing by the image processor 106 according to the present invention. These two images are referred to hereinafter as $I_{GE}$ and $I_{SE}$, and the magnitude of the signals at each of their respective pixels is referred to as $S_{GE}$ and $S_{SE}$.

Figure 4:
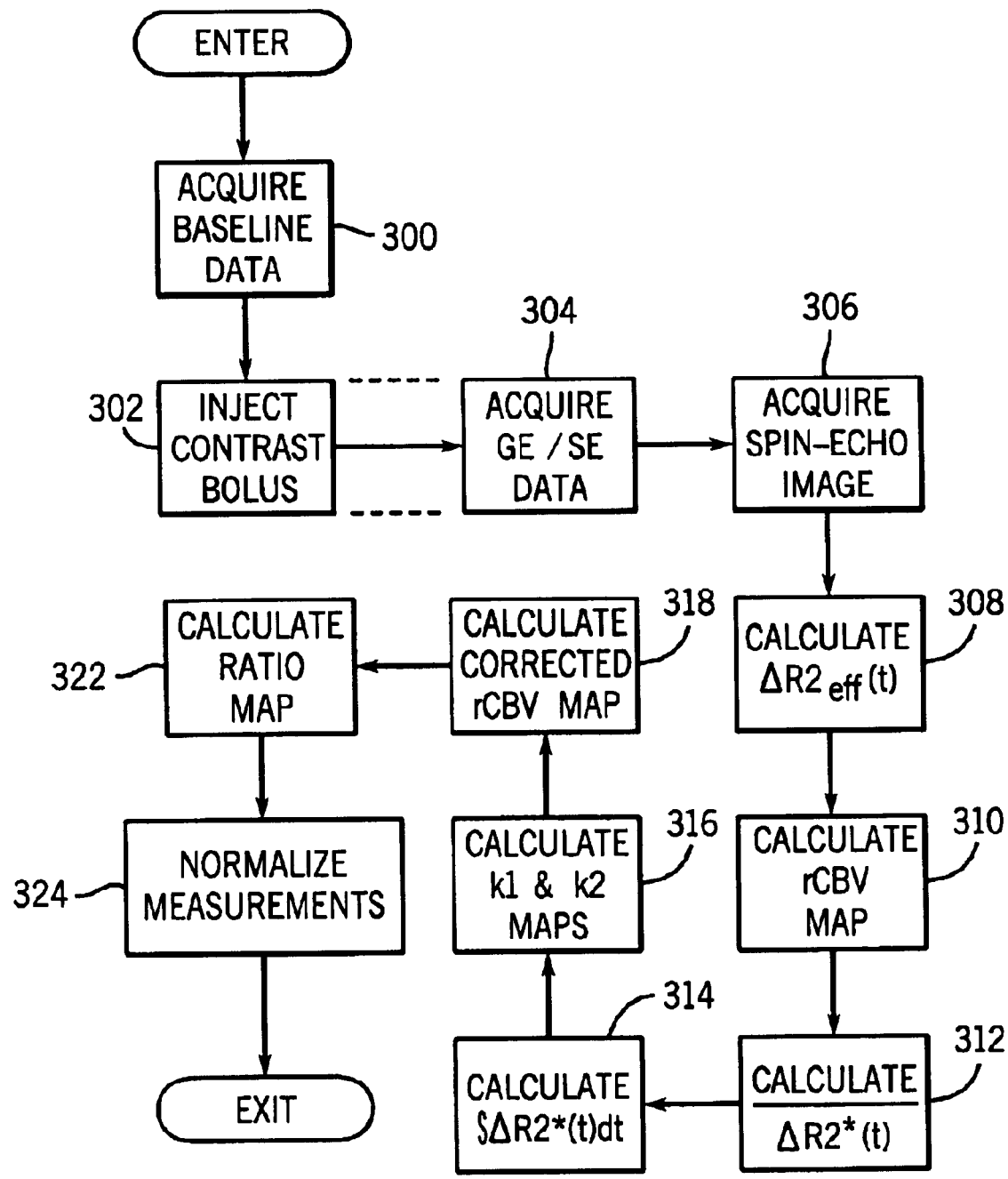
FIG. 4 is a flow chart of the preferred method for practicing the present invention.

Referring particularly to FIG. 4, to practice the present invention a dynamic study is conducted in which NMR data is acquired using the EPI pulse sequence of FIG. 3. Just prior to the dynamic imaging study, a 0.05 mmole/kg dose of Gadodiamide (Omniscan; Nycomed Amersham, Princeton N.J.) is administered to the patient to diminish T1 effects that might result from agent extravasation. If the initial tissue T1 is decreased with contrast agent, subsequent changes in T1, which might occur during the first-pass study, are minimized. An acquisition using the pulse sequence of FIG. 3 is then performed. During the first minute of this acquisition simultaneous GE/SE are acquired as indicated at process block 300. These serve as baseline images. A 0.15–0.25 mmole/kg bolus injection of contrast agent is performed as indicated at process block 302, and the acquisition of data continues using the pulse sequence of FIG. 3 for 1 to 2 minutes as indicated at process block 304. Five, 7 mm slices are acquired at $TE_{GE}$=30 ms and $TE_{SE}$=109.1 ms with fat suppression, a TR=1 s and a FOV=24 cm. Finally, conventional post-contrast T1-weighted images of the same slices are acquired with a spin-echo pulse sequence (SE, TE/TR= 11 ms/500 ms, matrix=256×256) as indicated at process block 306.

The simultaneously collected gradient echo and spin echo data are reconstructed into images $I_{GE}$ and $I_{SE}$ and divided into two data sets of time course data for each image slice. As will now be described, rCBV maps (corrected for agent extravasation), permeability-weighting (K2) maps, and transverse relaxation rate change ratio ($\Delta R2^*/\Delta R2$) maps are created from these two time course data sets.

The MR signal was modeled in terms of the combined T1 and T2-dominated effects of the Gadolinium contrast agent, as described by Weisskoff et al, "Simultaneous blood volume and permeability mapping using a single Gd-based contrast injection," $2^{nd}$ Annual Society of Magnetic Resonance, San Francisco, 279, 1994. The model for the gradient echo signal SGE is derived in the Appendix, and is expressed as follows:

$$\Delta R2^*_{eff}(t) = K1(x,y)\overline{\Delta R2^*(t)} - K2(x,y)\int_{T_{start}}^{t_{end}} \overline{\Delta R2^*(t)dt} \quad (1)$$

As indicated at process block 308, the effective change in the T2* relaxation rate $\Delta R2^*_{eff}(t)$ in the images $I_{GE}$ is determined for each image pixel at each time point in the time course data set as follows:

$$\Delta R2^*_{eff}(t) = -\left(\frac{1}{TE}\right)\ln\frac{S_{GE(t)}}{S_0} \quad (2)$$

where $S_{GE}(t)$ is the post-contrast signal for a pixel at time t and $S_O$ is the averaged pre-contrast baseline signal at the same pixel. Integration of the $\Delta R2^*_{eff}(t)$ values over the interval from 70 to 120 seconds during the time course study as indicated at process block 310 gives relative cerebral blood volume (rCBV) maps. These rCBV maps are uncorrected for leakage effects.

As indicated at process block 312, the $\overline{\Delta R2^*_{eff}(t)}$ term in Eq. 1 is determined next from the average of all pixel $\Delta R2^*_{eff}(t)$ values, in a given image, that did not demonstrate a steady-state signal enhancement greater than one standard deviation above the pixel's average baseline. These are the pixels that had no significant leakage of contrast agent. As indicated at process block 314, the cumulative sum (integral) of $\overline{\Delta R2^*_{eff}(t)}$ is determined using trapezoidal integration, with the integration limits set to just after contrast administration (at about 70 seconds) to 120 seconds. For each pixel, the $\Delta R2^*$ weighting (K1) and the permeability-weighting (K2) are determined using a linear least-squares fit to Eq. 1 as indicated at process block 316.

As indicated at process block 318, the next step is to calculate the corrected rCBV map. This is done by adding the uncorrected rCBV values to the permeability weighting factors K2 times the integral of the cumulative sum of $\overline{\Delta R2^*_{eff}(t)}$. Determination of each of these parameters on a pixel-by-pixel basis thus enables four image maps to be produced. (1) uncorrected $rCBV_{GE}$; (2) corrected $rCBV_{GE}$; (3) $\Delta R2^*$ weighting ($K1_{GE}$); and (4) permeability weighting ($K2_{GE}$).

The same calculations described above and indicated by process blocks 308–318 are repeated using the time course images $I_{SE}$ to produce four corresponding image maps: (1) $rCBV_{SE}$; (2) corrected $rCBV_{SE}$; (3) $\Delta R2$ weighting ($K1_{SE}$); and (4) permeability weighting ($K2_{SE}$).

Ratio maps are calculated using the $\Delta R2^*$ and $\Delta R2$ images as indicated at process block 322. The $T_2$ relaxation rate images ($\Delta R2^*$) are calculated as described above in Eq. 2 using the series of time course images reconstructed from acquired gradient-echo NMR signals. The transverse relaxation rate change images ($\Delta R2$) are calculated using the same Eq. 2, but with the series of images reconstructed from the acquired spin-echo NMR signals. Each pixel in a ratio map is calculated by averaging the ratios $\Delta R2^*/\Delta R2$ from corresponding pixels in ten images. The ten $T_2$ relaxation rate images are selected to encompass those produced from data acquired when blood contrast was at a maximum level after contrast bolus arrival. In the preferred embodiment this is detected by searching for the peak in the $\Delta R2^*$ values during the time course study.

Although all of the maps contain information regarding the imaged tumor, it is a discovery of the present invention that the corrected $rCBV_{GE}$ and corrected $rCBV_{SE}$ maps and the ratio map $\Delta R2^*/\Delta R2$ provide strong correlations with the tumor grade, which has been shown to correlate strongly with angiogenesis. Specifically, a strong statistical correlation was found between these MRI-derived measurements and the histopathologic tumor grade as determined with the Spearman rank correlation test, using p=0.05 as the significance threshold. To produce these measurements the data in respective $rCBV_{GE}$, $\Delta R2^*/\Delta R2$ and $rCBV_{SE}$ maps were extracted from ROIs placed both within the tumor, and contralateral brain. When delineating the tumor ROI, care was taken to avoid any obviously necrotic areas as apparent on the post-contrast, high-resolution, T1-weighting images that were acquired. The corrected tumor rCBV measurement and the ratio measurement results are presented as normalized to corresponding contralateral brain measurements as indicated at process block 324.

Noninvasive methods by which tumor vasculature can be evaluated are crucial for establishing clinical endpoints related to angiogenesis and the therapeutic efficacy of its inhibitors. Given that the progression of tumors from low grade to high grade is angiogenesis-dependent, with a clear correlation between increased vascularity and increased malignancy, these results support the hypothesis that the acquired GE/SE NMR information, derived with the methods described above, provide a measurement of both tumor angiogenesis and the efficacy of anti-angiogenic therapies. The corrected $rCBV_{GE}$ and $rCBV_{SE}$ measurements which reflect vessels of all sizes, and the $\Delta R2^*/\Delta R2$ ratio measurement are strongly associated with brain tumor grade.

Appendix

To create the rCBV and K2 maps the NMR signal is modeled in terms of the combined T1 and T2 or T2*-dominated effects of Gadolinium, as previously described by Weisskoff et al. The detailed derivation and assumptions of this model are described here for the case of the gradient echo NMR signal. The spin echo NMR signal model is similarly derived, with T2* and $\Delta R2^*$ replaced by T2 and $\Delta R2$ in the following equation.

The pre and post-contrast NMR signal can be written as:

$$S_{pre} = (1 - exp^{-TR/T2})e^{-TE/T2^*}$$

$$S(t)_{post} = (1 - exp^{-TR/T1(t)}{}_G)e^{-TE/T2^*(t)}{}_G \quad (A.1)$$

where T1 and T2* are the pre-gadolinium and $T1_G$ and $T2^*_G$ are the post-gadolinium ("G") relaxation times. By rewriting the post-contrast relaxation rates in terms of their relaxivity relationship $(1/T1_G = R1C_t + 1/T1;\ 1/T2^*_G = R2C_t + 1/T2^*)$ where Ct denotes tissue contrast agent concentration and R1 and R2 are the T1 and T2* relaxivities given in $mM^{-1}\ sec^{-1}$, the post-contrast signal intensity can be rewritten as follows:

$$S(t)_{post} = (1 - e^{-TR/T1}e^{-TR(R1C_t(t))})e^{-TE/T2^*}e^{-TE\Delta R2^*(t)} \quad (A.2)$$

The effective $\Delta R2^*$ ($\Delta R2^*_{eff}$) can then be determined from the logarithm of the ratio of the pre and post-contrast signal as follows:

$$\Delta R2^*_{eff}(t) = \frac{-1}{TE}\ln\left(\frac{S(t)_{post}}{S^*}\right) \quad (A.3)$$

Substitution of Eq. A.2 into Eq. A.3 gives:

$$\Delta R2^*_{eff}(t) = \frac{-1}{TE}\ln\left(\frac{(1 - e^{-TR/T1}e^{-TR(R1C_t(t))})e^{-TR/T2^*}e^{-TE\Delta R2^*(t)}}{(1 - e^{-TR/T1})e^{-TE/T2^*}}\right) \quad (A.5)$$

$$= \frac{-1}{TE}\left[\ln\left(\frac{(1 - e^{-TR/T1}e^{-TR(R1C_t(t))})}{(1 - e^{-TR/T1})}\right) + \ln(e^{-TE\Delta R2^*(t)})\right]$$

Assuming small T1-based enhancement (<30%, which is reasonable considering the initial loading dose and relatively long TR), and using the relationships $e^x \approx 1+x$ and $\ln((1+x) \approx X$ when $|x|<<1$, Eq. A.5 can be simplified to give:

$$\Delta R2^*_{eff}(t) = \Delta R2^*(t) - \frac{TR}{TE}\frac{e^{-TR/T1}}{(1 - e^{-TR/T1})}R1C_t(t) \quad (A.6)$$

Assuming that there is no back diffusion of Gd from the tissue space to the vascular space, the mass balance of the tissue Gd concentration can be expresses as:

$$\frac{dC_t(t)}{dt} = PS\overline{C_c(t)} = k\overline{\Delta R2^*(t)} \quad (A.7)$$

where PULSE SEQUENCE is the permeability-surface area product, is the average vascular concentration of Gd, $\overline{\Delta R2^*(t)}$ is the average $\Delta R2^*$, and k is PULSE SEQUENCE scaled by a contrast agent calibration factor. Integration of Eq. A.7 and substitution for $C_t(t)$ into Eq. A.6 gives the following formulation:

$$\Delta R2_{eff}(t) = \Delta R2^*(t) - \frac{TR}{TE}\frac{e^{TR/T2}}{(1 - e^{-TR/T1})}R1k\int\overline{\Delta R2^*(t)}dt \quad (A.8)$$

Next, $\Delta R2^*_{eff}(t)$ can be written in terms of the "T2" and "T1" dominant factors, each given as a function of the $\overline{\Delta R2^*(t)}$:

$$\Delta R2^*_{eff}(t) = K1(x, y)\overline{\Delta R2^*(t)} - K2(x, y)\int\overline{\Delta R2^*(t)}dt \quad (A.9)$$

where K1(x,y) and K2(x,y) are the $\Delta R2^*$ and permeability weighting factors. The $\overline{\Delta R2^*(t)}$ is computed by averaging $\Delta R2^*_{eff}(t)$ for all pixels that do not demonstrate signal enhancement greater than one standard deviation above the pixel's average baseline, while $\int\overline{\Delta R2^*(t)}dt'$ is computed from the cumulative sum of $\overline{\Delta R2^*(t)}$ using trapezoidal integration. The weighting factors are then determined for each pixel using a linear least-squares fit to Eq. A.9.

Finally, the CBV maps, corrected for agent leakage, are computed from the uncorrected CBV in each pixel (integration of $\Delta R2^*_{eff}(t)$) plus K2 times the integral of the cumulative sum of $\overline{\Delta R2^*(t)}$:

$$corrCBV(x, y) = uncorrCBV(x, y) + K2\int_{t_o}^{t_e}\sum\overline{\Delta R2^*(t)} \quad (A.10)$$

$$corrCBV(x, y) = \int_{t_o}^{t_e}\Delta R2^*_{eff} + K2\int_{t_o}^{t_e}\sum\overline{\Delta R2^*(t)} \quad (A.11)$$

where the limits of the integration are from just before ($t_o$) to about 40–50 seconds after contrast administration ($t_e$).

What is claimed is:

1. A method for producing an image of a patient's brain using a magnetic resonance imaging (MRI) system, the steps comprising:
   a) injecting a contrast agent which alters the T1 relaxation constant in blood flowing through the patient's brain;
   b) acquiring two time course image data sets using the MRI system during the first passage of the contrast agent through the patient's brain with a pulse sequence in which gradient-recalled NMR signals are acquired to form one time course image data set and in which spin-echo NMR signals are acquired to form a second time course image data set;
   c) producing a relative cerebral blood volume image (rCBV) using images reconstructed from NMR signals in one of the time course image data sets; and
   d) correcting the rCBV image for leakage of contrast agent out of the patient's vasculature.

2. The method as recited in claim 1 in which step d) is performed by:
   i) calculating from one of said time course image data sets a permeability weighting factor image (K2);
   ii) calculating from one of said time course image data sets a transverse relaxation rate change ($\Delta R2^*(t)$); and iii) combining the product of the results in steps i) and ii) with the rCBV image.

3. The method as recited in claim 2 in which step iii) is performed by multiplying values in the permeability weighting factor image (K2) by the results calculated in step ii) and adding the result to the rCBV image.

4. The method as recited in claim 1 in which the pulse sequence is an echo-planar imaging pulse sequence.

5. The method as recited in claim 1 in which step c) is performed using the gradient-recalled NMR signals.

6. The method as recited in claim 5 which includes:

e) producing a second relative cerebral blood volume imaging (rCBVSE) using images reconstructed from the spin-echo NMR signals in the other one of the time course image data sets; and f) correcting the second rCBVSE image for leakage of contrast agent out of the patient's vasculature.

7. The method as recited in claim 6 which includes:

g) calculating a set of T2 relaxation rate images from the one time course image data set;

h) calculating a second set of T2 relaxation rate images from the other one of the time course image data sets; and i) calculating a ratio image by averaging the ratios of corresponding values in the first and second set of T2 relaxation rate images.

\* \* \* \* \*